United States Patent
Lee et al.

(10) Patent No.: US 9,820,806 B2
(45) Date of Patent: Nov. 21, 2017

(54) SWITCH ASSEMBLY FOR ELECTROSURGICAL INSTRUMENT

(75) Inventors: Weng-Kai K. Lee, Longmont, CO (US); Jeffrey R. Townsend, Loveland, CO (US); Scott N. LaCosta, Lafayette, CO (US); Jason T. Sanders, Johnstown, CO (US); Grant T. Sims, Littleton, CO (US)

(73) Assignee: Covidien LP, Mansfield, MA (US)

( * ) Notice: Subject to any disclaimer, the term of this patent is extended or adjusted under 35 U.S.C. 154(b) by 1491 days.

(21) Appl. No.: 12/569,395

(22) Filed: Sep. 29, 2009

(65) Prior Publication Data

US 2011/0077648 A1 Mar. 31, 2011

(51) Int. Cl.
*A61B 18/14* (2006.01)
*A61B 18/00* (2006.01)
*A61B 18/12* (2006.01)

(52) U.S. Cl.
CPC ............ *A61B 18/1445* (2013.01); *A61B 2018/00916* (2013.01); *A61B 2018/00922* (2013.01); *A61B 2018/00952* (2013.01); *A61B 2018/00958* (2013.01); *A61B 2018/1246* (2013.01)

(58) Field of Classification Search
CPC .......... A61B 2018/00916; A61B 2018/00922; A61B 2018/00952; A61B 2018/00958; A61B 2018/1246; A61B 18/1445
USPC ......................... 606/41, 42, 50–52
See application file for complete search history.

(56) References Cited

U.S. PATENT DOCUMENTS

| D263,020 S | 2/1982 | Rau, III |
| 4,427,006 A | 1/1984 | Nottke |
| 4,463,234 A | 7/1984 | Bennewitz |
| 4,595,809 A | 6/1986 | Pool |
| D295,893 S | 5/1988 | Sharkany et al. |
| D295,894 S | 5/1988 | Sharkany et al. |

(Continued)

FOREIGN PATENT DOCUMENTS

| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley
*Assistant Examiner* — Samantha Good

(57) ABSTRACT

An electrosurgical forceps includes a housing having a shaft affixed thereto, the shaft including jaw members at a distal end thereof. The forceps also includes a switch assembly that includes a supporting member, a flexible membrane circuit having snap dome switch contacts operably fixed thereto, and ergonomically-contoured keytops. The switch assembly provides at least one monopolar activation switch, and a bipolar activation switch. The forceps also include a drive mechanism which causes the jaw members to move relative to one another for manipulating tissue. A monopolar safety switch is incorporated into the switch assembly which cooperates with the drive mechanism to inhibit the monopolar activation switch when the jaw members are in an open position.

6 Claims, 14 Drawing Sheets

(56) References Cited

U.S. PATENT DOCUMENTS

| | | | |
|---|---|---|---|
| 4,827,927 | A | 5/1989 | Newton |
| 4,916,275 | A | 4/1990 | Almond |
| 5,098,430 | A | 3/1992 | Fleenor |
| 5,306,238 | A | 4/1994 | Fleenor |
| D348,930 | S | 7/1994 | Olson |
| 5,401,273 | A | 3/1995 | Shippert |
| 5,512,721 | A | 4/1996 | Young et al. |
| 5,562,720 | A | 10/1996 | Stern et al. |
| 5,601,601 | A | 2/1997 | Tal et al. |
| D384,413 | S | 9/1997 | Zlock et al. |
| 5,911,719 | A | 6/1999 | Eggers |
| 6,024,743 | A | 2/2000 | Edwards |
| D424,694 | S | 5/2000 | Tetzlaff et al. |
| D425,201 | S | 5/2000 | Tetzlaff et al. |
| D449,886 | S | 10/2001 | Tetzlaff et al. |
| D457,958 | S | 5/2002 | Dycus et al. |
| D457,959 | S | 5/2002 | Tetzlaff et al. |
| 6,545,239 | B2 | 4/2003 | Spedale et al. |
| 6,747,218 | B2 | 6/2004 | Huseman et al. |
| D493,888 | S | 8/2004 | Reschke |
| D496,997 | S | 10/2004 | Dycus et al. |
| D499,181 | S | 11/2004 | Dycus et al. |
| D509,297 | S | 9/2005 | Wells |
| 6,977,495 | B2 | 12/2005 | Donofrio |
| 7,041,102 | B2 | 5/2006 | Truckai et al. |
| D525,361 | S | 7/2006 | Hushka |
| D531,311 | S | 10/2006 | Guerra et al. |
| 7,115,123 | B2 | 10/2006 | Knowlton et al. |
| D533,942 | S | 12/2006 | Kerr et al. |
| D535,027 | S | 1/2007 | James et al. |
| 7,156,842 | B2 | 1/2007 | Sartor et al. |
| 7,156,844 | B2 | 1/2007 | Reschke et al. |
| D541,418 | S | 4/2007 | Schechter et al. |
| D541,938 | S | 5/2007 | Kerr et al |
| 7,267,677 | B2 | 9/2007 | Johnson et al. |
| 7,329,256 | B2 | 2/2008 | Johnson et al. |
| D564,662 | S | 3/2008 | Moses et al. |
| D567,943 | S | 4/2008 | Moses et al. |
| D575,395 | S | 8/2008 | Hushka |
| D575,401 | S | 8/2008 | Hixson et al. |
| 7,513,898 | B2 | 4/2009 | Johnson et al. |
| 2004/0030332 | A1 | 2/2004 | Knowlton et al. |
| 2006/0052779 | A1 | 3/2006 | Hammill |
| 2006/0064086 | A1 | 3/2006 | Odom |
| 2006/0178667 | A1 | 8/2006 | Sartor et al. |
| 2007/0049926 | A1 | 3/2007 | Sartor |
| 2007/0078456 | A1 | 4/2007 | Dumbauld et al. |
| 2007/0093810 | A1 | 4/2007 | Sartor et al. |
| 2007/0106297 | A1 | 5/2007 | Dumbauld et al. |
| 2007/0156139 | A1 | 7/2007 | Schechter et al. |
| 2007/0173814 | A1 | 7/2007 | Hixson et al. |
| 2007/0213708 | A1 | 9/2007 | Dumbauld |
| 2007/0260241 | A1 | 11/2007 | Dalla Betta et al. |
| 2007/0282335 | A1* | 12/2007 | Young et al. ............ 606/50 |
| 2008/0114356 | A1 | 5/2008 | Johnson et al. |
| 2008/0249523 | A1 | 10/2008 | McPherson |
| 2008/0249527 | A1 | 10/2008 | Couture |
| 2008/0281311 | A1 | 11/2008 | Dunning |
| 2008/0319442 | A1 | 12/2008 | Unger et al. |
| 2009/0012520 | A1 | 1/2009 | Hixson et al. |
| 2009/0048596 | A1 | 2/2009 | Shields et al. |
| 2009/0171353 | A1 | 7/2009 | Johnson et al. |
| 2009/0182327 | A1 | 7/2009 | Unger |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/060849 | 7/2005 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparoscopic Surgery; Sales/Product Literature; Apr. 2002.

(56) References Cited

OTHER PUBLICATIONS

Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al."Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534dated Dec. 19, 2003.
Int'l Search Report PCT/US04/03436 dated Mar. 3, 2005.

(56) References Cited

OTHER PUBLICATIONS

Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
International Search Report EP10181969 dated Feb. 4, 2011.
Canadian Office Action dated Jul. 20, 2016, issued in Canadian Application No. 2,715,927.
European Office Action dated Aug. 30, 2017, issued in EP Application No. 10181969.

* cited by examiner

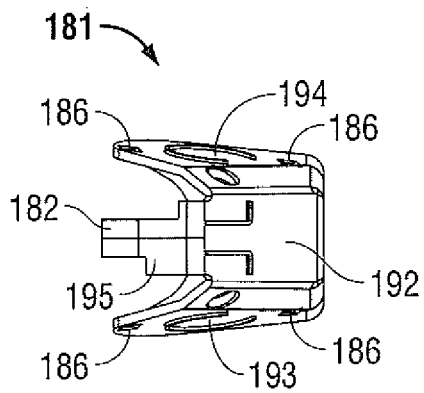
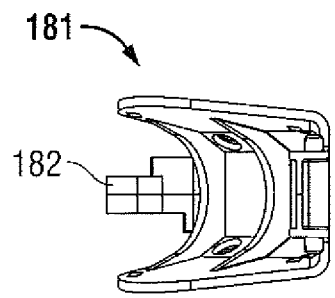
FIG. 4D    FIG. 4E
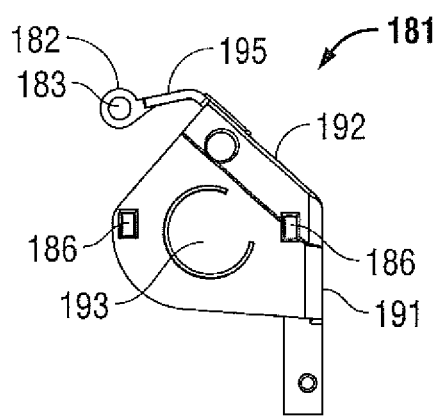
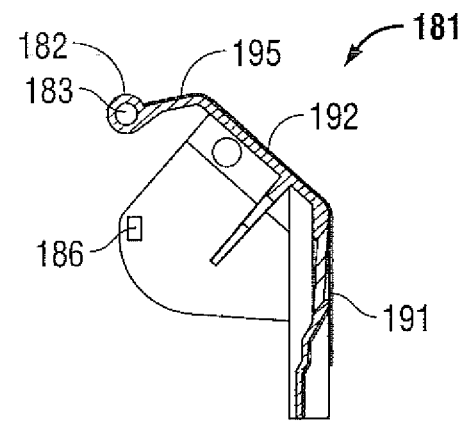
FIG. 4F    FIG. 4G

SWITCH ASSEMBLY FOR ELECTROSURGICAL INSTRUMENT

BACKGROUND

1. Technical Field

The present disclosure relates to an electrosurgical forceps, and, more particularly, the present disclosure relates to an endoscopic electrosurgical forceps for sealing and/or cutting large tissue structures.

2. Background of Related Art

Electrosurgical forceps utilize both mechanical clamping action and electrical energy to affect hemostasis by heating the tissue and blood vessels to coagulate, cauterize and/or seal tissue. Many surgical procedures require cutting and/or ligating large blood vessels and large tissue structures. Due to the inherent spatial considerations of the surgical cavity, surgeons often have difficulty suturing vessels or performing other traditional methods of controlling bleeding, e.g., clamping and/or tying-off transected blood vessels or tissue. By utilizing an elongated electrosurgical forceps, a surgeon can either cauterize, coagulate/desiccate, dissect, and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, larger vessels can be more difficult to close using these standard techniques.

In order to resolve many of the known issues described above and other issues relevant to cauterization and coagulation, a technology was developed by Valleylab, Inc. of Boulder, Colo., a division of Tyco Healthcare LP (now Covidien—Energy Based Devices) called vessel or tissue sealing. The process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass with limited demarcation between opposing tissue structures. Coagulation of small vessels is sufficient to permanently close them, while larger vessels and tissue need to be sealed to assure permanent closure.

In order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal.

Providing an instrument which consistently provides the appropriate closure force between opposing electrode within a preferred pressure range will enhance the chances of a successful seal. It has been found that the pressure range for assuring a consistent and effective seal for large vessels and tissue structures is between about 3 kg/cm2 to about 16 kg/cm2 and, desirably, within a working range of 7 kg/cm2 to 13 kg/cm2. As can be appreciated, manufacturing an instrument which is capable of consistently providing a closure pressure within these working ranges is quite a design challenge for instrument manufacturers.

It may be necessary for a surgeon to perform both vessel sealing and dissection during certain surgical procedures. In such procedures, a greater number of instruments may be required to achieve the surgical objective. The use of greater numbers of instruments may affect surgical outcomes, due in part to the need to perform instrument changes in which additional time is used to withdraw one instrument, to prepare a subsequent instrument for use, and to manipulate the subsequent instrument into position for performing the required surgical steps.

SUMMARY

An electrosurgical instrument is herein disclosed having the capability of being selectively operated in a monopolar mode and/or a bipolar mode. The disclosed instrument includes a housing having a shaft affixed thereto. The shaft includes a longitudinal axis defined therethrough and a pair of end effectors, e.g., jaw members, disposed at a distal end thereof. The end effectors are adapted to selectively connect to a source of electrosurgical energy such that the end effectors are capable of supplying energy in a monopolar mode wherein energy flows from the instrument, through tissue, and to a return pad positioned on the patient, and, additionally or alternatively, wherein the end effectors are capable of supplying energy in a bipolar wherein energy is conducted through tissue held therebetween to affect tissue sealing. A switch assembly provided by the instrument housing is adapted to selectively activate monopolar energy and/or bipolar energy. The disclosed instrument includes at least one momentary pushbutton switch that is configured to activate bipolar energy, and at least one momentary pushbutton switch that is configured to activate monopolar energy. In an envisioned embodiment, the disclosed instrument includes two monopolar activation pushbutton positioned on opposite sides of the handle to facilitate ambidextrous operation of the instrument.

In an embodiment, the disclosed instrument includes a switch assembly disposed within the instrument housing. The switch assembly includes a switch carrier that includes a handle pivot mount which may be integrally formed therewith. A generally cruciform flex circuit assembly is positioned on an exterior surface of the switch housing. The flex circuit assembly includes at least one snap dome switch disposed on a multi-layer flexible printed circuit membrane. A snap dome switch is a momentary switch contact that, when used in conjunction with a printed circuit board, flex circuit, or membrane, forms a normally-open tactile switch. Metal domes may be placed on a substrate printed circuit board, flex circuit, or membrane circuit board by means of pressure-sensitive adhesive tape. In their relaxed state, the metal domes rest on the outer rim of an outer contact. When pushed, the dome collapses and establishes contact between the outer contact and an inner contact, thereby completing an electrical circuit. Actuation of a snap dome switch therefore causes electrical continuity to be established between corresponding traces provided by the circuit membrane. An edge connector provided by the flex circuit assembly enables circuit traces to be operatively coupled in electrical communication with, e.g., a source of electrosurgical energy such as without limitation an electrosurgical generator and/or a controller thereof. A wire harness may be provided within the instrument handle that is adapted to operably couple the flex circuit assembly edge connector to a connection cable. The connection cable may extend at least in part from the exterior of the instrument housing. Additionally or alternatively, the wire harness may be integrally formed with the connection cable. The flex circuit assembly includes at least two resistive circuit elements arranged to form a voltage dividing network that is adapted to cause an activation signal having a predetermined voltage to be generated in response to actuation of a snap dome switch. The switch assembly may include at least one ergonomic keytop configured to extend through a corresponding opening defined in the instrument housing which couples actuation force from, e.g., a finger of a user, to an underlying snap dome switch on the circuit membrane.

The instrument includes a movable handle which is rotatable about a pivot to force a drive flange of the drive assembly to move the jaw members between the first and second positions. A selectively advanceable knife assembly is included having a knife bar which moves a knife to cut tissue between jaw members. A knife lockout mechanism operatively connects to the drive assembly. Movement of the drive assembly moves the lockout mechanism from a first orientation in obstructive relationship with the knife bar to prevent movement thereof to a second position which allows selective, unencumbered movement of the knife bar to cut tissue disposed between the jaw members.

In another aspect, the disclosed instrument includes a monopolar activation lockout that is configured to inhibit monopolar mode activation when the end effector, e.g., jaws, are in a first (e.g., open) position. A monopolar safety switch is included within the switch assembly. A cam provided by the movable handle engages the safety switch when the movable handle is in the second (e.g., closed) position thereby enabling the activation of monopolar energy.

A drive assembly having a selectively advanceable drive sleeve is configured to move the jaw members relative to one another from a first position wherein the jaw members are disposed in spaced relation relative to one another to a second position wherein the jaw members are closer to one another for manipulating tissue.

In one embodiment, the drive assembly includes a drive stop disposed near the proximal end thereof. The drive stop is operatively engaged with the knife lockout mechanism such that selective movement of the drive assembly causes the drive stop to move or rotate the knife lockout mechanism between the first position and the second position.

In another embodiment, the knife bar includes a generally t-shaped proximal end dimensioned to operatively engage a corresponding slot defined within the housing. The slot configured to guide the movement of the knife bar during translation thereof. The knife lockout mechanism may be dimensioned to obstruct the t-shaped proximal end of the knife bar when disposed in the first position. The knife assembly may include a cuff at the distal end of the knife bar which is dimensioned to encapsulate and move atop the drive sleeve upon movement of the knife bar.

In yet another embodiment, the knife bar is operatively coupled to a knife slidingly disposed within the shaft and the forceps further includes a finger actuator operatively coupled to the knife assembly. Movement of the finger actuator moves the knife bar which, in turn, moves the knife to cut tissue disposed between the jaw members.

A finger actuator may be operatively connected to the knife assembly. The finger actuator includes two generally u-shaped flanges which rotate about a pivot to abut and force the cuff distally which, in turn, results in distal translation of the knife bar. A spring may also be included which biases the knife assembly in a proximal-most orientation. A spring may also be included which biases the knife lockout mechanism in the first position.

Another embodiment of the present disclosure includes a housing having a shaft affixed thereto. The shaft includes a longitudinal axis defined therethrough and a pair of jaw members disposed at a distal end thereof. The jaw members are adapted to connect to a source of electrosurgical energy such that the jaw members are capable of conducting energy through tissue held therebetween to affect a tissue seal. A drive assembly having a selectively advanceable drive sleeve is configured to move the jaw members relative to one another from a first position wherein the jaw members are disposed in spaced relation relative to one another to a second position wherein the jaw members are closer to one another for manipulating tissue.

A movable handle is included which is rotatable about a pivot to force a drive flange of the drive assembly to move the jaw members between the first and second positions. The pivot is located a fixed distance above the longitudinal axis and the drive flange is located generally along the longitudinal axis. A knife assembly is included which has a knife bar with a t-shaped proximal end. The knife assembly is selectively movable to advance the knife bar which, in turn, moves a knife to cut tissue between jaw members.

A knife lockout mechanism operatively connects to the drive assembly. Movement of the drive sleeve of the drive assembly pivots the knife lockout mechanism between a first orientation in obstructive relationship with the t-shaped proximal end of the knife bar to prevent movement thereof to a second position which allows selective, unencumbered movement of the t-shaped proximal end of the knife bar to reciprocate the knife to cut tissue disposed between the jaw members.

In one aspect, the present disclosure provides an electrosurgical switch assembly that includes a switch carrier and a flex circuit assembly disposed on an exterior surface of the switch carrier. The flex circuit includes at least one monopolar switch configured to selectively activate a source of monopolar electrosurgical energy. Also included is a monopolar safety switch that is designed to enable (e.g., enable activation of) the at least one monopolar switch when the monopolar safety switch is actuated. The switch assembly also includes a bipolar switch that is configured to selectively activate a source of bipolar electrosurgical energy.

Also disclosed is an electrosurgical forceps and system, comprising a housing having a shaft affixed thereto. The shaft includes jaw members at a distal end thereof that are configured to move relative to one another from a first (e.g., open) position, wherein the jaw members are disposed in spaced relation relative to one another, to a second (e.g., closed) position wherein the jaw members are closer to one another for manipulating tissue. A switch assembly as described herein is included within the housing. The electrosurgical forceps and system includes a movable handle configured to cause the jaw members to move between the first and second positions and to actuate the monopolar safety switch when the jaw members are in the second position. The disclosed electrosurgical forceps and system may additionally include a source of electrosurgical energy, which may be configured to provide monopolar electrosurgical energy and/or bipolar electrosurgical energy.

Also disclosed is a method for performing electrosurgery, comprising the steps of providing an electrosurgical forceps that includes a housing having a shaft affixed thereto. the shaft includes jaw members at a distal end thereof, a drive mechanism which causes the jaw members to move relative to one another between an open position to a closed position for manipulating tissue, and a switch assembly that includes a supporting member and a flexible membrane circuit having a monopolar activation switch, a bipolar activation switch, and a monopolar safety switch. A determination is made as to whether the jaw members are in a closed position or an open position. If the jaw members are in a closed position, the monopolar activation switch is enabled (e.g., made ready for use), while if the jaw members are not in a closed position (e.g., in an open position), the monopolar activation switch is disabled.

BRIEF DESCRIPTION OF THE DRAWINGS

Various embodiments of the subject instrument are described herein with reference to the drawings wherein:

FIG. 4D is a top view of a switch assembly carrier in accordance with the present disclosure;

FIG. 4E is a bottom view of a switch assembly carrier in accordance with the present disclosure;

FIG. 4F is a side view of a switch assembly carrier in accordance with the present disclosure;

FIG. 4G is a side, cutaway view of a switch assembly carrier in accordance with the present disclosure;

DETAILED DESCRIPTION

Figure 1A:
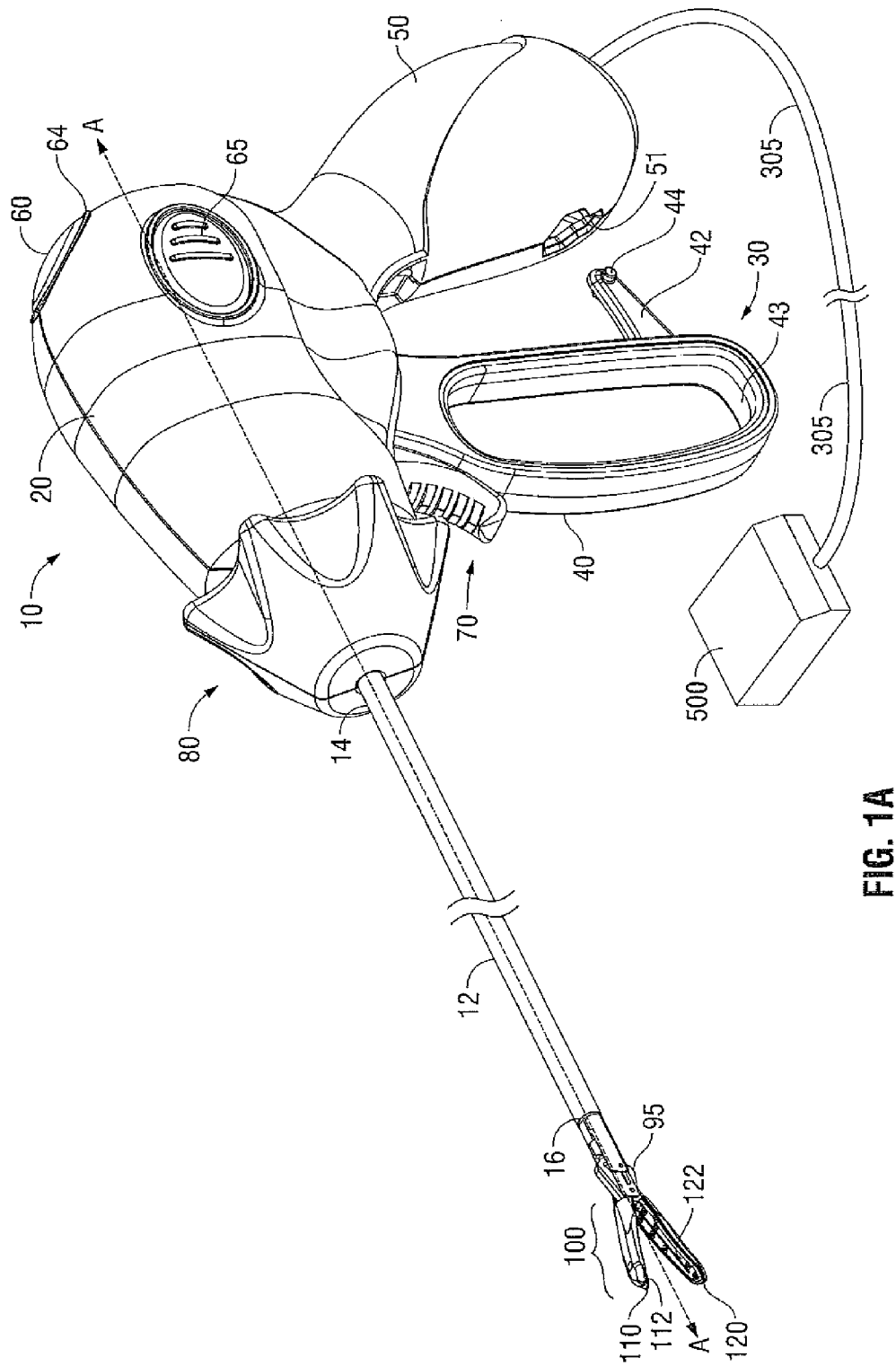
FIG. 1A is a perspective view of a bipolar forceps shown in open configuration and including a housing, a shaft, a handle assembly, a movable handle, a trigger assembly, a button assembly, and an end effector assembly according to the present disclosure.

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the terms "proximal", as is traditional, shall refer to the end of the instrument that is closer to the user, while the term "distal" shall refer to the end that is farther from the user.

Turning now to FIGS. 1A, 1B, 2A, and 2B, an embodiment of a forceps 10 is shown. The forceps 10 is adapted for use in various surgical procedures and generally includes a housing 20, a handle assembly 30, a rotating assembly 80, a trigger assembly 70, a switch assembly 180, and an end effector assembly 100 which mutually cooperate to grasp, seal and divide large tubular vessels and large vascular tissues. Although the majority of the figure drawings depict a forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

Forceps 10 includes a shaft 12 that has a distal end 16 dimensioned to mechanically engage the end effector assembly 100 and a proximal end 14 that mechanically engages the housing 20. The proximal end 14 of shaft 12 is received within the housing 20.

Forceps 10 also includes an electrosurgical cable 305 that connects the forceps 10 to a source of electrosurgical energy, e.g., a generator 500 (shown schematically). It is contemplated that generators such as those sold by Valleylab, Inc. (now Covidien), may be used as a source of electrosurgical energy, e.g., Ligasure™ Generator, FORCE EZ™ Electrosurgical Generator, FORCE FX™ Electrosurgical Generator, FORCE 1CT™, FORCE 2™ Generator, SurgiStat™ II or other envisioned generators which may perform different or enhanced functions. One such system is described in commonly-owned U.S. Pat. No. 6,033,399 entitled "ELECTROSURGICAL GENERATOR WITH ADAPTIVE POWER CONTROL". Other systems have been described in commonly-owned U.S. Pat. No. 6,187,003 entitled "BIPOLAR ELECTROSURGICAL INSTRUMENT FOR SEALING VESSELS".

In one embodiment, the generator 500 includes various safety and performance features including isolated output, independent activation of accessories. It is envisioned that the electrosurgical generator includes Covidien's Instant Response™ technology features which provides an advanced feedback system to sense changes in tissue 200 times per second and adjust voltage and current to maintain appropriate power. The Instant Response™ technology is believed to provide one or more of the following benefits to surgical procedure, including consistent clinical effect through all tissue types; reduced thermal spread and risk of collateral tissue damage; less need to "turn up the generator"; and is well-adapted to the minimally invasive environment.

Cable 305 is internally divided into control leads (not explicitly shown) that are adapted to transmit electrical potentials through their respective feed paths through the forceps 10 to the switch assembly 180. Cable 305 may additionally or alternatively include energy leads (not explicitly shown) that are designed to transmit electrical potentials through their respective feed paths through the forceps 10 to the end effector assembly 100. Details relating to the electrical connections are explained in more detail below with the discussion of the switch assembly 180.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10 and switch assembly 180. Fixed handle 50 is oriented approximately 30 degrees relative a longitudinal axis A-A defined through shaft 12. Fixed handle 50 may include one or more ergonomic enhancing elements to facilitate handling, e.g., scallops, protuberances, elastomeric material, etc. Rotating assembly 80 is operatively associated with the housing 20 and is rotatable approximately 180 degrees about a longitudinal axis A-A (See FIG. 1A).

As mentioned above, end effector assembly 100 is attached at the distal end 14 of shaft 12 and includes a pair of opposing jaw members 110 and 120. Movable handle 40 of handle assembly 30 is operably coupled to a drive assembly 130 which, together, mechanically cooperate to impart movement of the jaw members 110 and 120 from a first (e.g., open) position, wherein the jaw members 110 and 120 are disposed in spaced relation relative to one another, to a second (e.g., clamping or closed position), wherein the jaw members 110 and 120 cooperate to grasp tissue therebetween.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12, and/or the proximal end 14 of shaft 12 may be selectively and releasably engageable with the housing 20 and the handle assembly 30. In either of these two instances, the forceps 10 would be considered "partially disposable" or "reposable", e.g., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

Turning now to the more detailed features of the present disclosure as described with respect to FIGS. 1A, 1B, 2A, and 2B, movable handle 40 includes a finger loop 43 which has an aperture 41 defined therethrough which enables a user to grasp and move the handle 40 relative to the fixed handle 50. Finger loop 43 is typically ergonomically enhanced and may include one or more gripping elements (not shown) disposed along the inner peripheral edge of aperture 41 which are designed to facilitate gripping of the movable handle 40 during activation, e.g., a so-called "soft touch" or elastomeric material. Gripping elements may include one or more protuberances, scallops and/or ribs to enhance gripping.

Figure 1B:
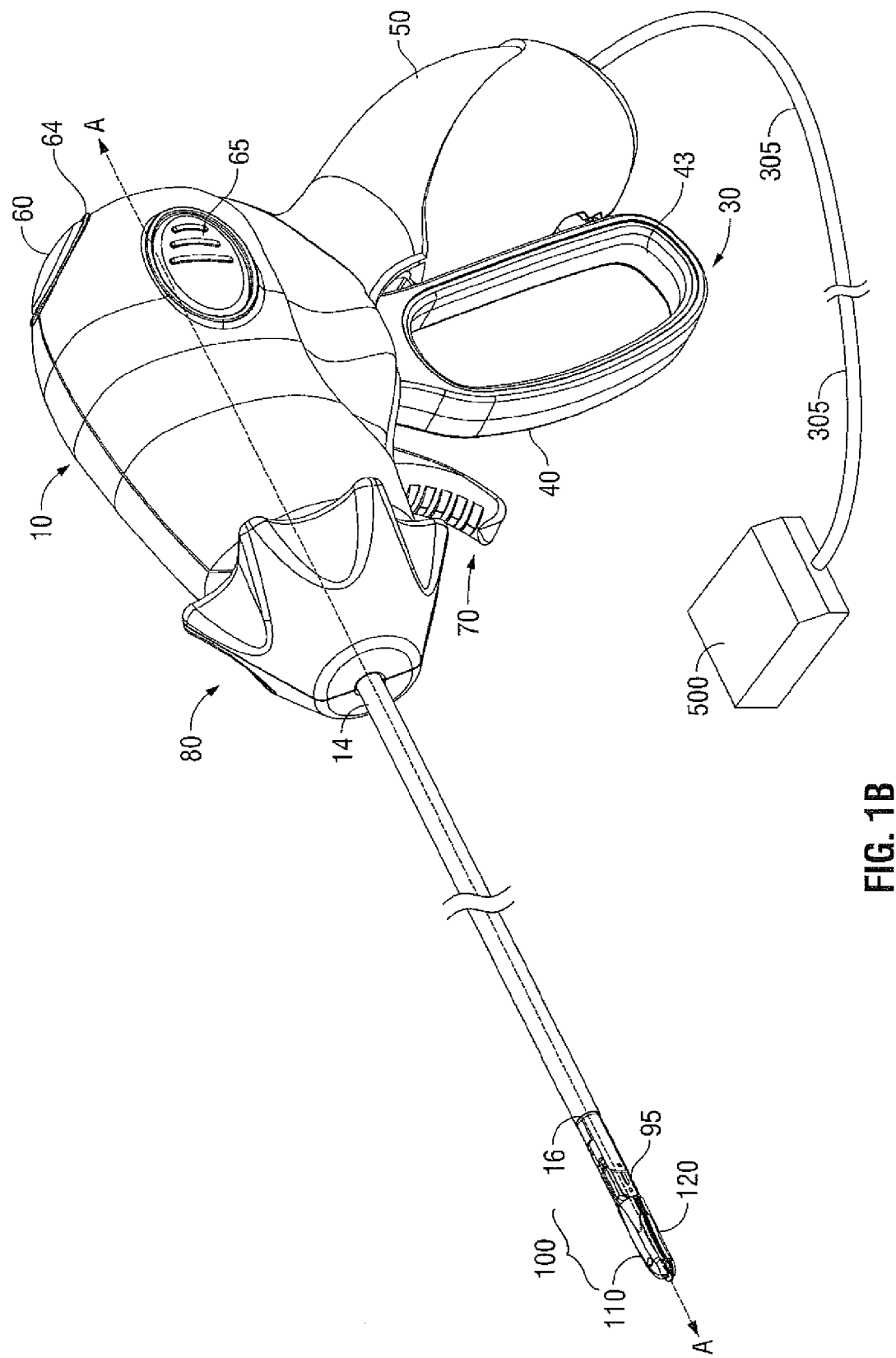
FIG. 1B is a perspective view of the bipolar forceps of FIG. 1A shown in closed configuration.
Figure 2A:
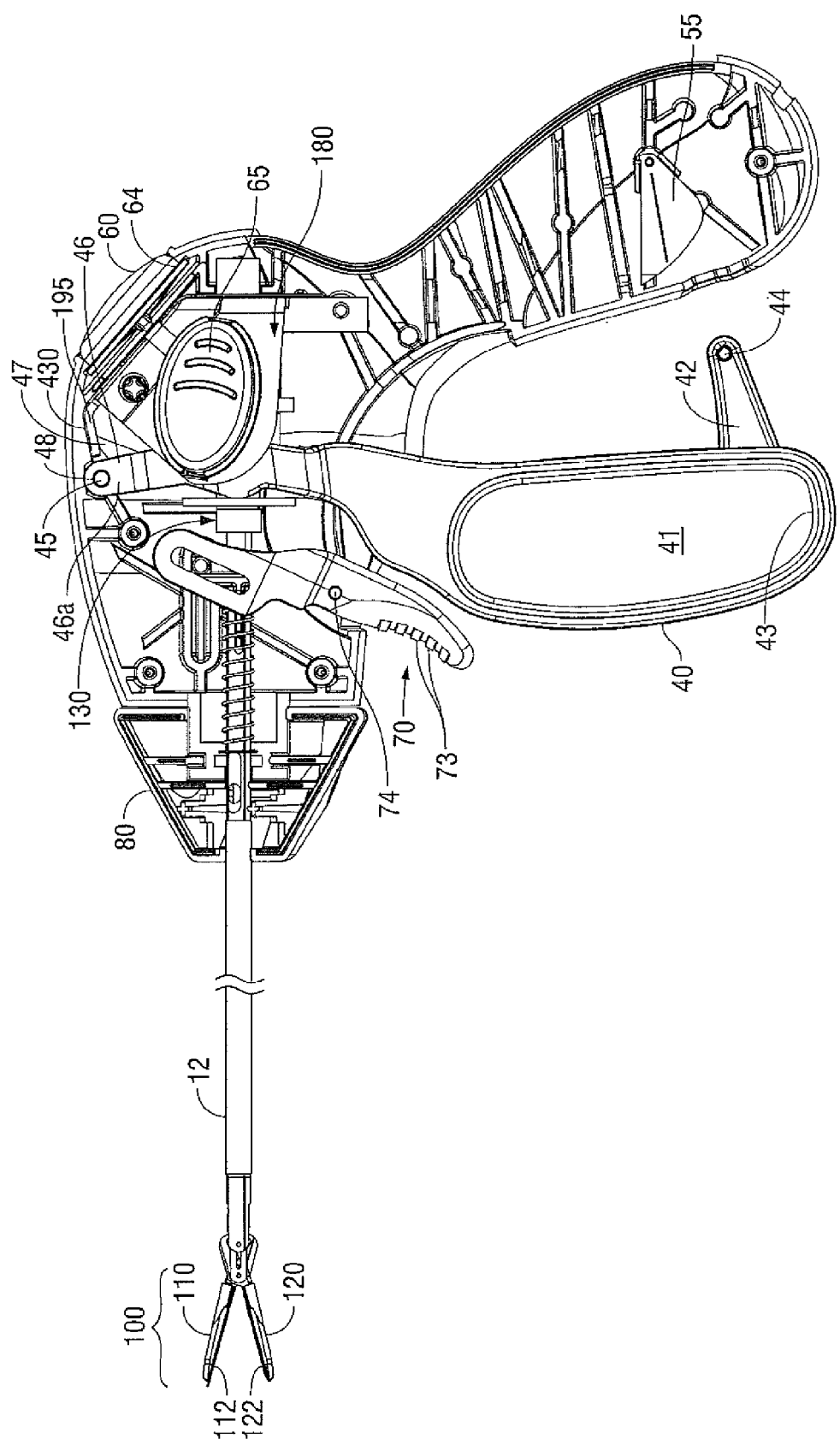
FIG. 2A is a side, cutaway view of the forceps of FIG. 1A shown in an open configuration.
Figure 2B:
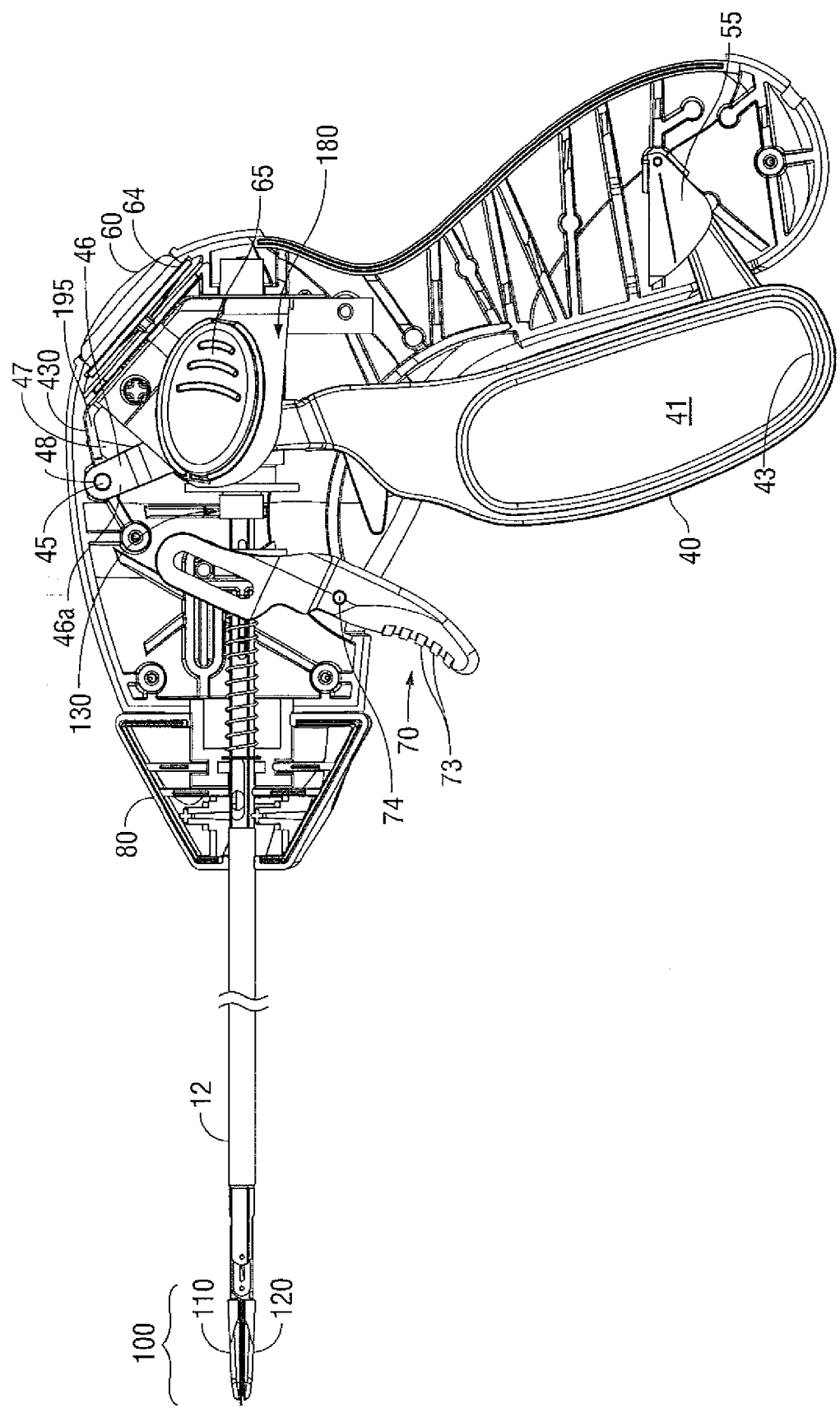
FIG. 2B is a side, cutaway view of the forceps of FIG. 1A shown in a closed configuration.
Figure 3A:
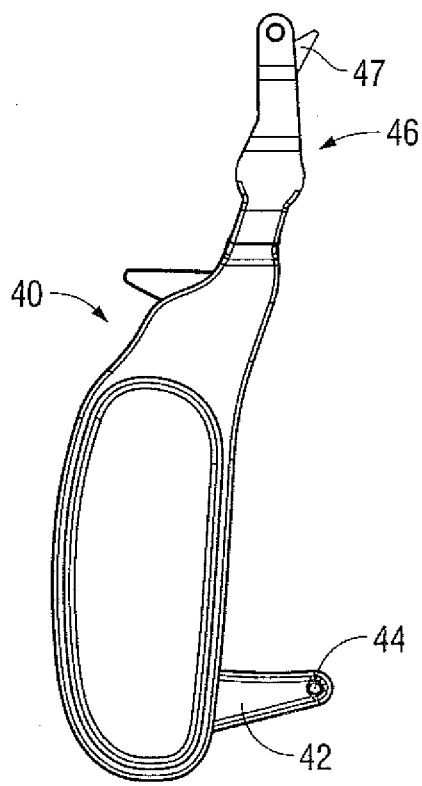
FIG. 3A is side view of a handle assembly in accordance with the present disclosure.
Figure 3B:
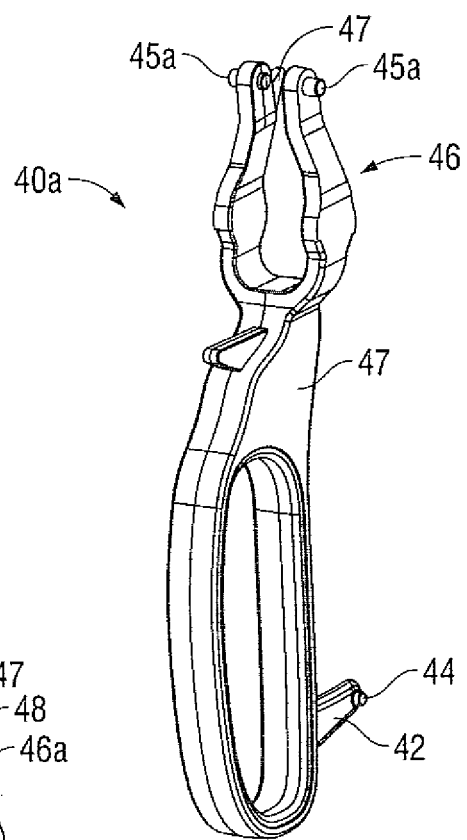
FIG. 3B is perspective view of a handle assembly in accordance with the present disclosure.
Figure 3C:
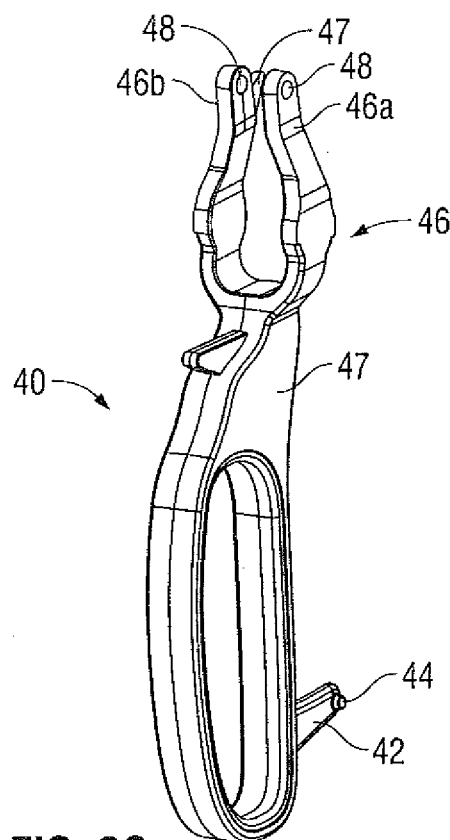
FIG. 3C is perspective view of another handle assembly in accordance with the present disclosure.
Figure 4A:
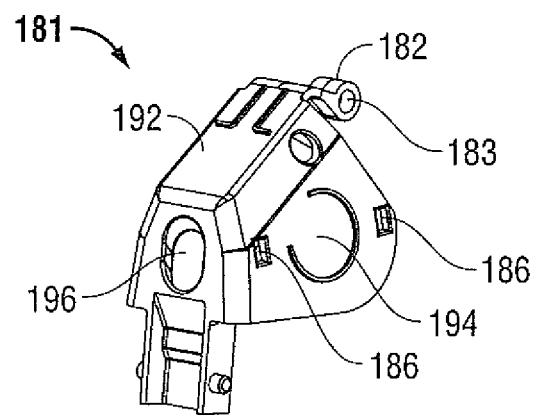
FIG. 4A is a perspective view of a switch assembly carrier in accordance with the present disclosure.
Figure 4B:
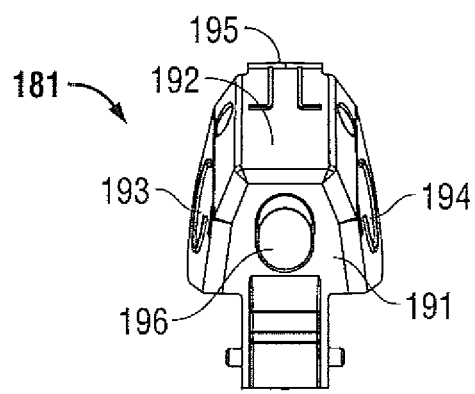
FIG. 4B is a top, rear view of a switch assembly carrier in accordance with the present disclosure.
Figure 4C:
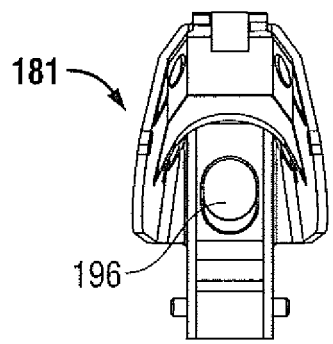
FIG. 4C is a bottom, front view of a switch assembly carrier in accordance with the present disclosure.
Figure 5A:
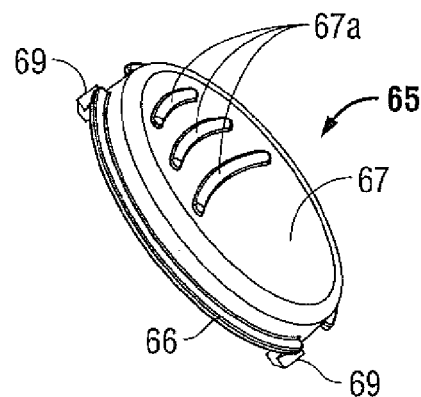
FIG. 5A is a perspective view of a monopolar switch keytop in accordance with the present disclosure.
Figure 5B:
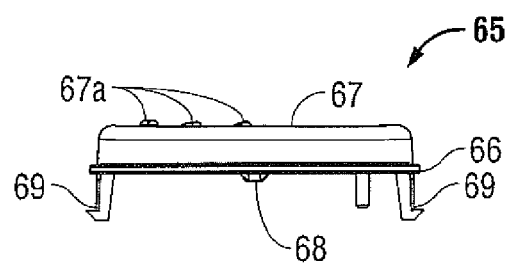
FIG. 5B is a side view of the monopolar switch keytop of FIG. 5A.
Figure 6A:
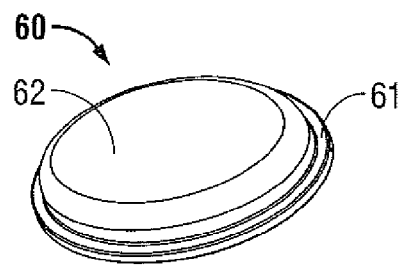
FIG. 6A is a perspective view of a bipolar switch keytop in accordance with the present disclosure.
Figure 6B:
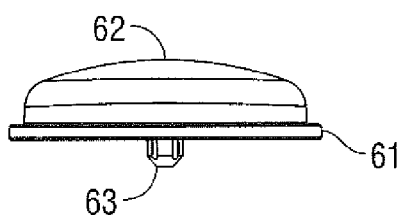
FIG. 6B is a side view of the bipolar switch keytop of FIG. 6A.
Figure 7:
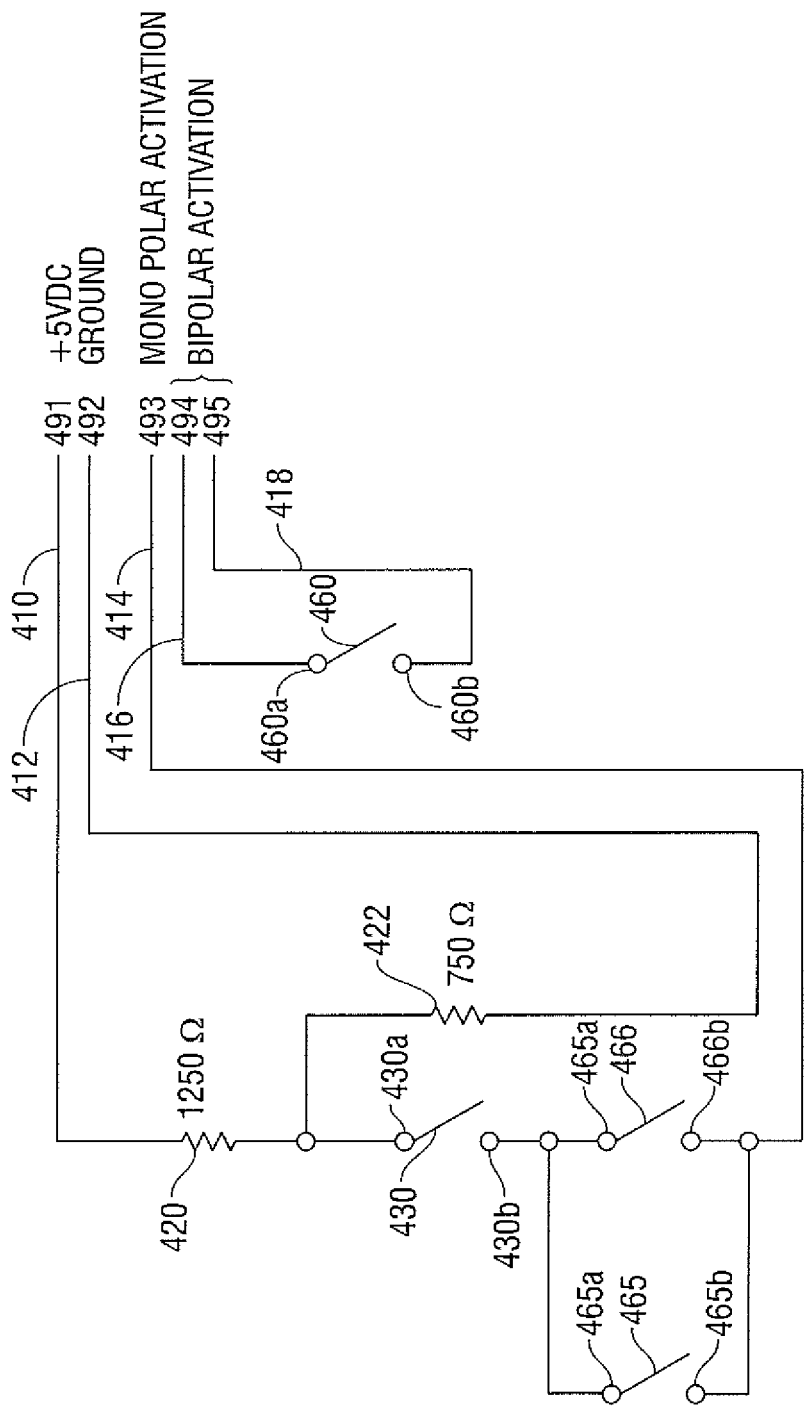
FIG. 7 is a electrical schematic diagram of a switch assembly in accordance with the present disclosure.

Referring to FIGS. 2A and 2B, movable handle 40 is selectively movable about a pivot pin 45 from a first position relative to fixed handle 50 (as shown in FIGS. 1A and 2A) to a second position (as shown in FIGS. 1B and 2B) in closer proximity to the fixed handle 50 which, by operative association with drive assembly 130, imparts movement of the jaw members 110 and 120 relative to one another. Referring to FIGS. 3A and 3C, movable handle 40 includes a clevis 46 that forms a pair of upper flanges 46a and 46b each having an aperture 48 at an upper end thereof for receiving the pivot pin 45 therethrough and mounting the upper end of the handle 40 relative to the switch assembly 180. In turn, pivot pin 45 mounts to switch housing 181 (FIG. 4A-4C) at pivot mount 182. Pivot pin 45 is dimensioned to mount within a transverse opening 183 defined in pivot mount 182. In an embodiment, a pivot pin 45a may be integrally formed with handle 40a, as best seen in FIG. 3B. At least one of upper flange 46a or 46b also includes a cam lobe 47 positioned at a proximal edge thereof, which, when assembled, abuts the switch assembly 180 such that pivotal movement of the handle 40 drives cam lobe 47 toward and, ultimately, in contact with, monopolar safety switch 430, which, in turn, closes monopolar safety switch 430 and enables activation of monopolar energy upon actuation of a monopolar activation switch 465, 466.

Referring to FIGS. 4A-4G, FIG. 8D, and FIG. 10, switch assembly 180 includes switch carrier 181, a flex circuit assembly 200 mounted on the carrier 181, and one or more keytop 60, 65. Switch carrier 181 has a roughly saddle-shaped construction, having a top-proximal face 192, a left face 193, a right face 194, a top face 195, and a proximal face 191. The switch carrier 181 may be formed from any suitable material, including without limitation, liquid crystal polymer (LCP), e.g., Vectra A430, manufactured by Ticona of Florence, Ky., USA. Faces 192, 193, 194 and 195 of switch carrier 181 are configured to support switch contacts 460, 465, 466, and 430, respectively, that are included with flex circuit 200. An opening 196 is defined in proximal face 191 which may provide support to a proximal end of drive assembly 130. At least one retention opening 186 is defined in each of left face 193 and right face 194 to receive retention clip 69 of keytop 65.

Figure 8A:
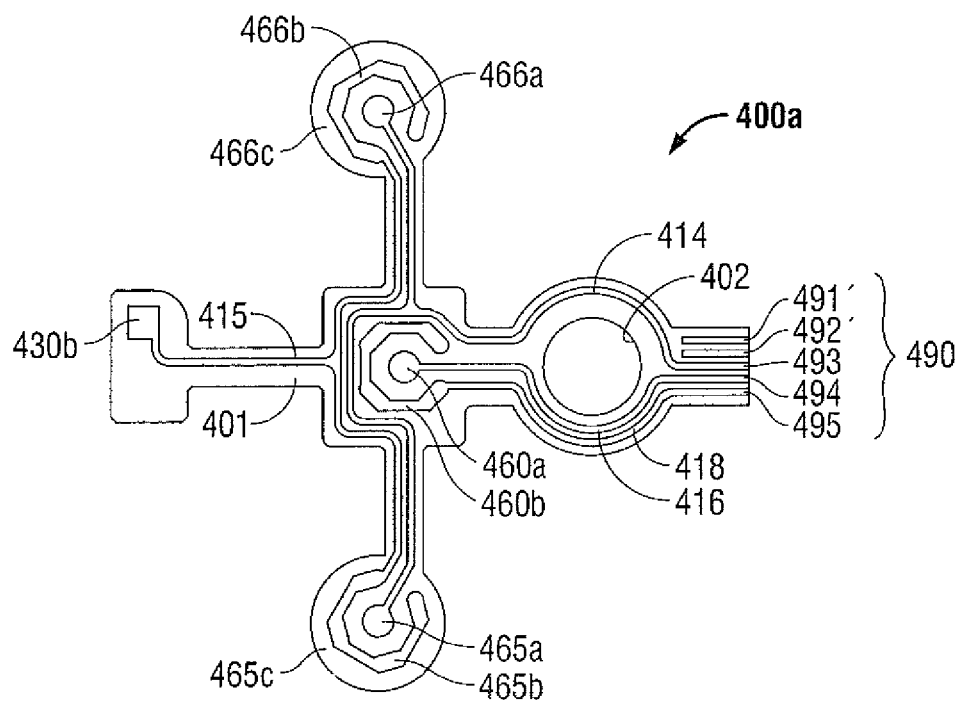
FIG. 8A is a view of a bottom circuit layer of a flex circuit assembly in accordance with the present disclosure.
Figure 8B:
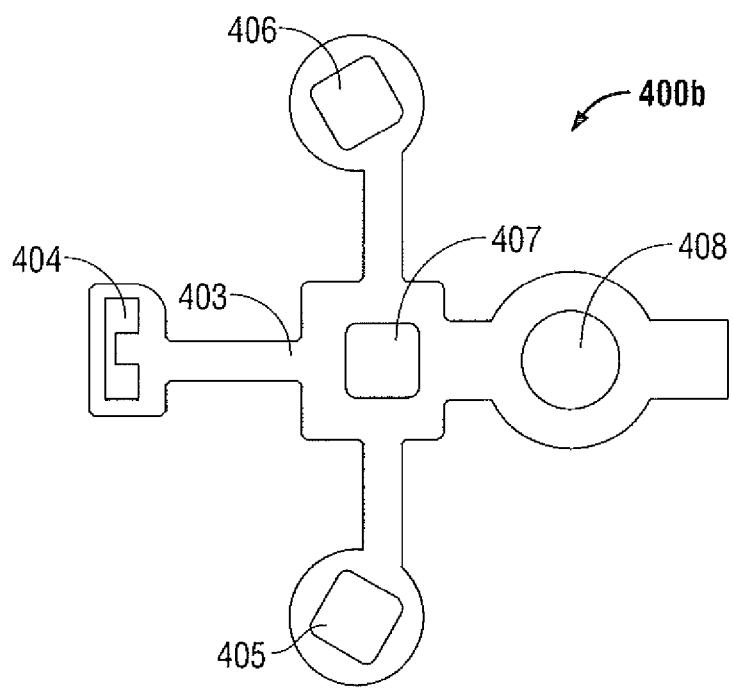
FIG. 8B is a view of an adhesive spacer layer of a flex circuit assembly in accordance with the present disclosure.
Figure 8C:
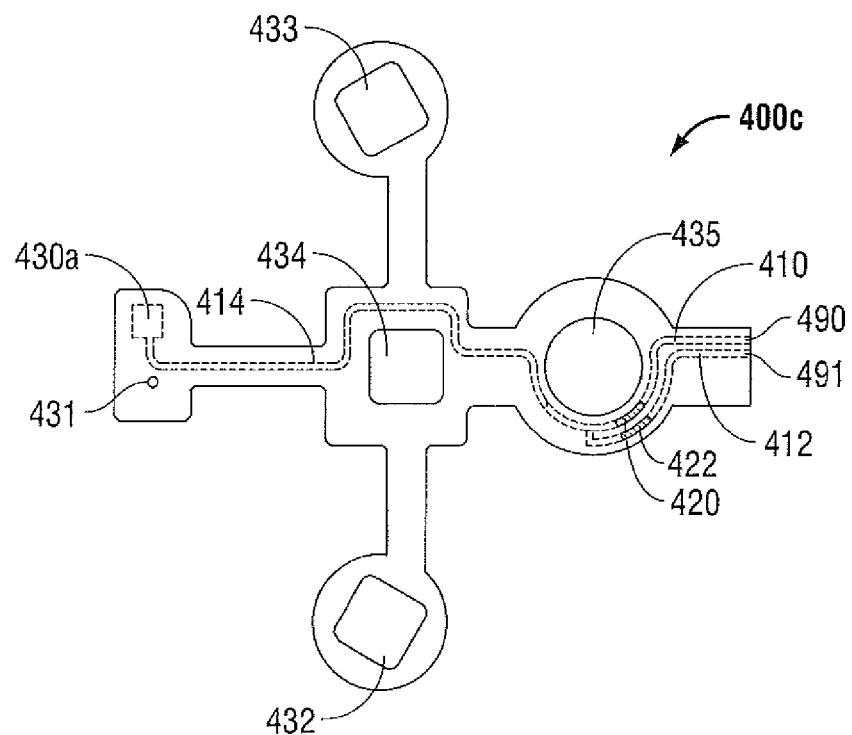
FIG. 8C is a view of a top circuit layer of a flex circuit assembly in accordance with the present disclosure.
Figure 8D:
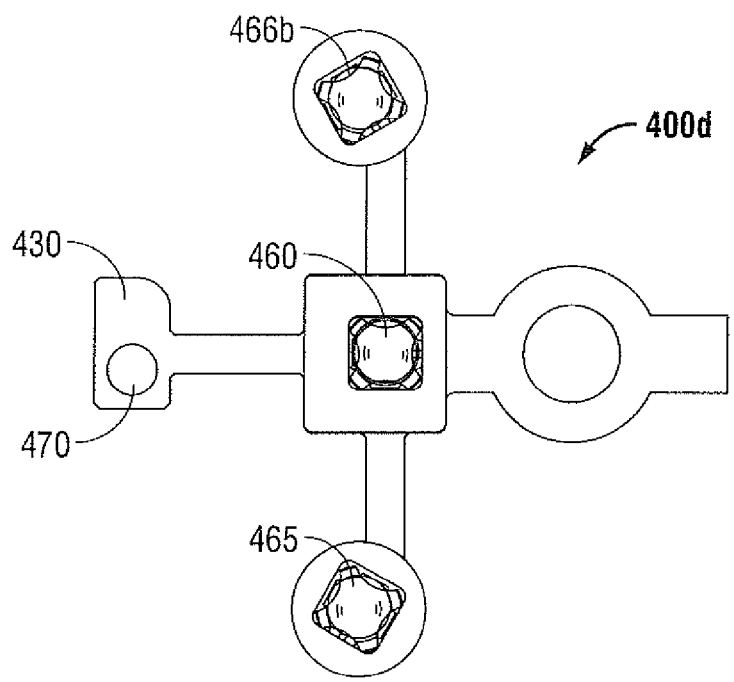
FIG. 8D is a view of a flex circuit assembly in accordance with the present disclosure.

With reference to FIGS. 7, 8A-8D and 9, flex circuit assembly 200 includes a bottom circuit layer 400a, an adhesive layer 400b, and a top circuit layer 400c, each having a generally cruciform shape. Bottom circuit layer 400a, adhesive layer 400b, and/or top circuit layer 400c may be formed in part by die-cutting, laser-cutting, CNC cutting machines, and/or any suitable manner of fabrication. Bottom circuit layer 400a includes a substrate 401 and at least one circuit trace and/or contact pad disposed thereupon as best seen in FIG. 8A. Substrate 401a may be formed from any suitable non-conductive material, such as without limitation polyimide, e.g., Kapton™ film manufactured by E, I. du Pont de Nemours and Company of Wilmington, Del., United States. Substrate 401 may have any suitable thickness, however, it is envisioned that substrate 401 has a thickness of about 0.005 inches. Circuit traces 416, 418 are arranged to electrically couple inner bipolar contact pad 460a and outer bipolar contact pad 460b, respectively, to corresponding terminals 494 and 495 of edge connector 490. Circuit trace 414 is arranged to couple left monopolar inner contact pad 465a and right monopolar inner contact pad 466a in common with terminal 493 of edge connector 490. Circuit trace 415 is arranged to couple left monopolar outer contact pad 465b and right monopolar outer contact pad 466b in common with bottom safety switch contact pad 430b. A generally circular opening 402, having a diameter roughly corresponding to opening 196, is defined in substrate 401. The circuit traces as described herein may be formed from any suitable conductive material, including without limitation #5025 silver conductive ink manufactured by E. I. du Pont de Nemours and Company. A dielectric coating (not explicitly shown), such as without limitation, #5018 UV-curable coating manufactured by E. I. du Pont de Nemours and Company, may be selectively applied to the non-contact pad portions of the circuit traces.

Adhesive layer 400b includes an adhesive substrate 403 that may be formed from any suitable adhesive and/or adhesive film-backed material, such as without limitation, double-sided adhesive tape, e.g., #7953 MP adhesive tape, manufactured by 3M of St. Paul, Minn., United States. Adhesive substrate 403 includes a plurality of openings 404, 405, 406, 407, and 408 defined therein: a generally circular opening 408, having a diameter roughly corresponding to opening 196; a pair of substantially square opening 405 and 406 that are each adapted to accommodate monopolar snap dome switches 465 and 466, respectively; a substantially square opening 407 that is adapted to accommodate bipolar snap dome switch 460, and a generally U-shaped opening 404 that is configured to provide a deformation region (not explicitly shown) which enables contact between bottom safety switch contact pad 430b and top safety switch contact pad 430a during actuation thereof. Opening 404 additionally may provide fluidic coupling between the deformation region (not explicitly shown) to the atmosphere via vent opening 431 of top circuit layer 400c to accommodate the reduced volume of the deformation region during actuation, e.g., when bottom safety switch contact pad 430b and top safety switch contact pad 430a are brought into electrical communication in response to force applied thereto by cam lobe 47 of handle 40.

Top circuit layer 400c includes circuit trace 410 that is arranged to couple edge contact 490 to resistor 420, and circuit trace 412 that is arranged to couple edge contact 491 to resistor 422. Resistors 420 and/or 422 may be formed from any suitable resistive material, such as without limitation, M3012-1 and/or M3013-1 RS carbon blend material manufactured by Minico/Asahi Chemical, of Congers, N.Y. United States. Resistors 420 and 422 form a voltage divider network to provide a reference voltage to top safety switch contact pad 430a via circuit trace 414. In an embodiment, resistor 420 has a value of about 1,250Ω and resistor has a value of about 750Ω. Top circuit layer 400c has defined therein a pair of substantially square openings 432 and 433, each adapted to accommodate a monopolar snap dome switch as described below, a substantially square opening 434 that is adapted to accommodate a bipolar snap dome switch as described below, a generally circular opening 435 having a diameter roughly corresponding to opening 196, and a vent opening 431. A cover 470 is fixed in a generally centered fashion over vent opening 431. Vent cover 470 may be formed from liquid-resistant, gas-permeable material, such as without limitation, Gore™ Series VE4, manufactured by W. L. Gore & Associates, Inc. of Newark, Del., United States.

Figure 9:
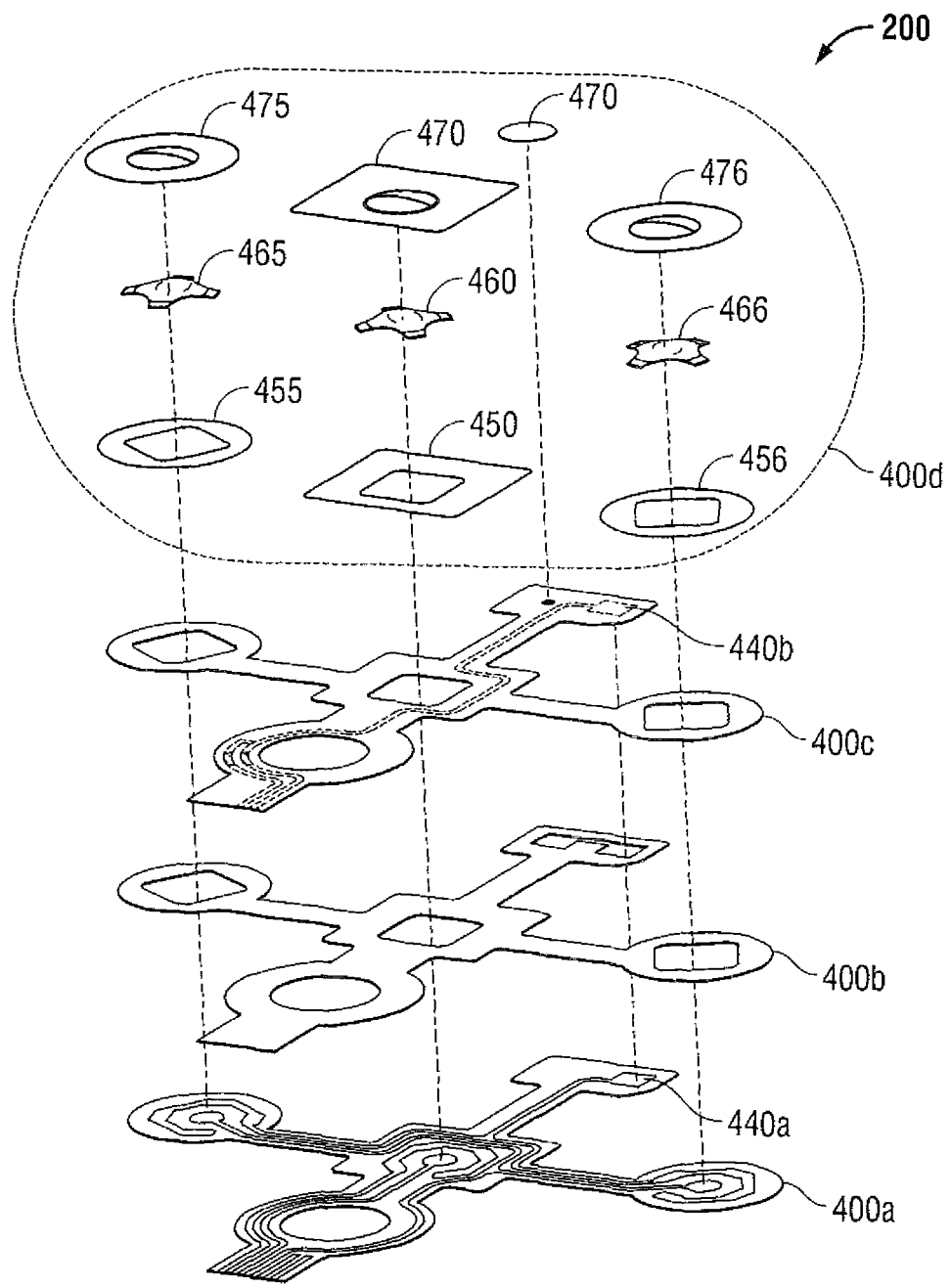
FIG. 9 is an exploded view of a flex circuit assembly in accordance with the present disclosure.

Bottom circuit layer 400a, adhesive layer 400b, and top circuit layer 400c, and switch layer 400d are assembled as shown in FIG. 9 to form flex circuit assembly 200. Bottom circuit layer 400a, is joined to top circuit layer 400c by adhesive layer 400b. Snap dome switch 460 is joined to bottom circuit layer 400a in a sandwich fashion by the combination of bipolar dome retainer 470, which captures snap dome switch 460 against bottom circuit layer 400a, and bipolar dome adhesive layer 450, which fixes bipolar dome retainer 470 and snap dome switch 460 in position over inner bipolar contact pad 460a and outer bipolar contact pad 460b. By this configuration, deformation of snap dome switch 460 in response to actuation pressure establishes electrical continuity between inner bipolar contact pad 460a and outer bipolar contact pad 460b

Monopolar snap dome switches 465, 466 are joined to bottom circuit layer 400a in a similar fashion to the respective positions thereof, e.g., snap dome switch 465 is joined to bottom circuit layer 400a by monopolar dome adhesive layer 455 and monopolar dome retainer 475, and snap dome switch 466 is joined to bottom circuit layer 400a by monopolar dome adhesive layer 456 and monopolar dome retainer 476. In an embodiment snap dome switches 460, 465, and/or 466 may be a Snaptron F08400N snap dome switch having a 400 gram actuation pressure (a.k.a., "trip force"), however, the use of any suitable snap dome contact is contemplated within the scope of the present disclosure.

Figure 10:
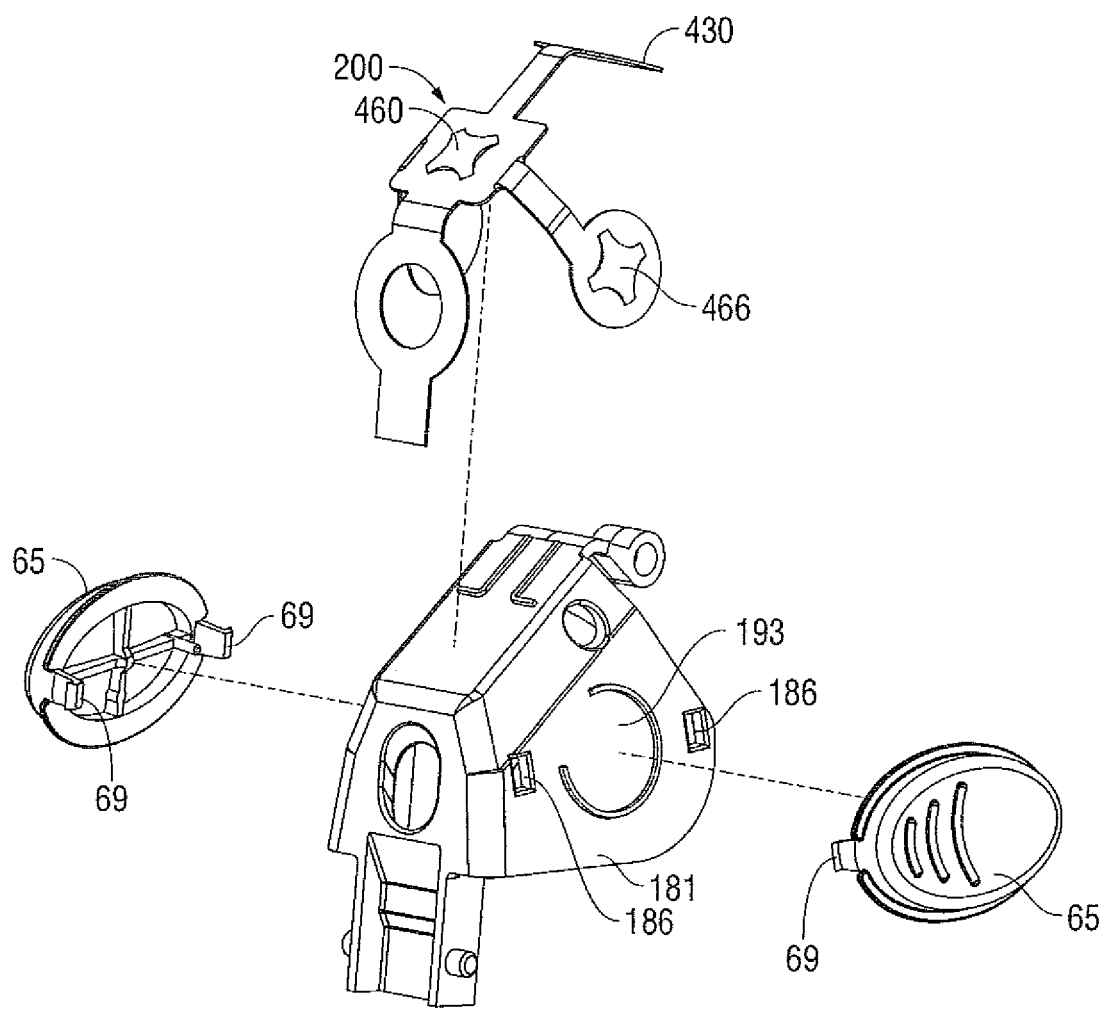
FIG. 10 is an exploded view of a switch assembly in accordance with the present disclosure.
Figure 11:
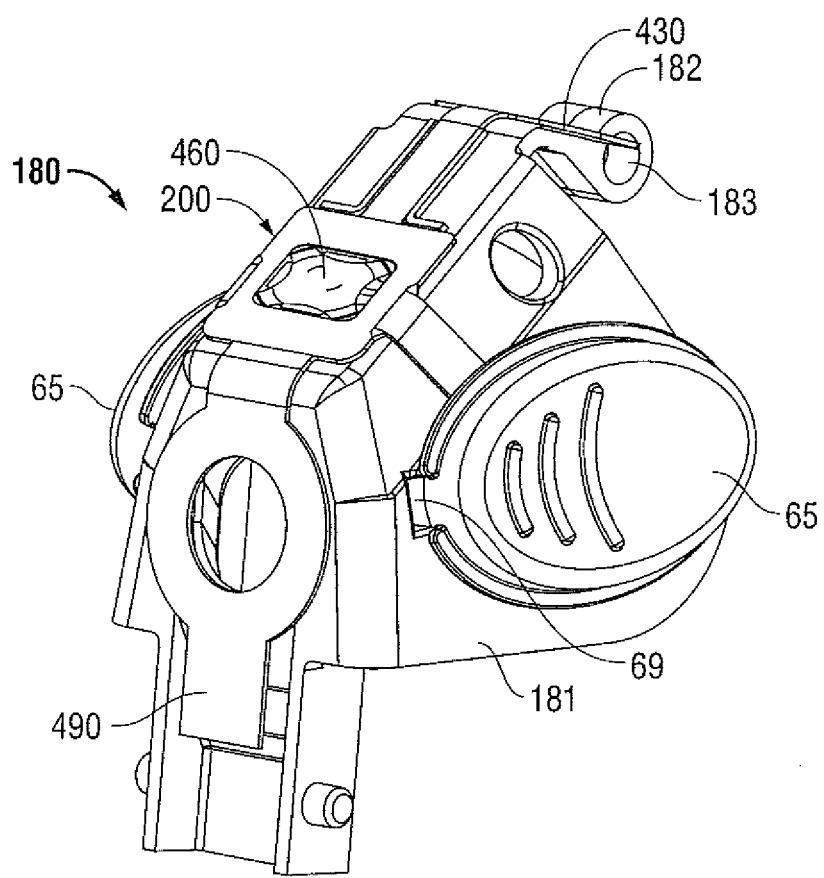
FIG. 11 is a perspective view of a switch assembly in accordance with the present disclosure.

Referring now to FIGS. 10 and 11, flex circuit assembly 200 is disposed upon switch carrier 181 such that bipolar snap dome switch 460 is disposed on top-proximal face 192, monopolar snap dome switch 465 is disposed on left face 193, monopolar snap dome switch 466 is disposed on right face 194, and safety switch 430 is disposed on top face 195. As best seen in FIGS. 10 and 11, the cruciform appendages of flex circuit assembly 200 are flexed to conform generally to the shape of carrier 181. Flex circuit assembly 200 may be fixed to carrier 181 by any suitable manner of attachment, including without limitation, adhesive, and/or laser welding. A monopolar keytop 65 is operably coupled to carrier 181 by engagement of retention clips 69 with retention opening 186. Nub 68 is substantially aligned with a center of the corresponding snap dome switch 465, 466 and is adapted to transfer actuation force from keytop 65 to the underlying snap dome switch 465, 466.

Bipolar keytop 60 is disposed within an opening 64 defined within the housing 20 (FIGS. 1A and 2A). Opening 64 is dimensioned to enable the top portion 62 of bipolar keytop 60 to move freely therein, e.g., inwardly and outwardly with respect to housing 20 and underlying bipolar snap dome switch 460. Bipolar keytop 60 is retained within opening 64 by shoulder 61 of bipolar keytop 60. Nub 63 is substantially aligned with a center of the bipolar snap dome switch 460 and is adapted to transfer actuation force from bipolar keytop 60 to the underlying bipolar snap dome switch 460.

Switch assembly 180 is disposed within housing 20 and configured to electromechanically cooperate with drive mechanism 130, handle 40, and bipolar keytop 60 to allow a user to selectively activate the jaw members 110 and 120 in a monopolar and/or bipolar mode. Monopolar safety switch 430 is configured such that the monopolar activation switches 65 are disabled when the handle 40 and/or jaw members 110 and 120 are in an open position, and/or when jaw members 110 and 120 have no tissue held therebetween (FIGS. 2A and 2B). When handle 40 is in an open position, e.g., distal position, cam 47 is effectively disengaged from monopolar safety switch 430 causing bottom safety switch contact pad 430b and top safety switch contact pad 430a to remain separated, causing an open circuit thereby inhibiting operation of either monopolar switch 465, 466. When handle 40 is in a closed, e.g., proximal, position, cam 47 engages bottom safety switch 430 by deforming a region of flex circuit substrate region, causing contact pad 430b to electrically couple with top safety switch contact pad, establishing a closed circuit path which enables monopolar switch 465, 466, upon actuation thereof, to provide a monopolar activation signal to, e.g., generator 500 via cable 305. Actuation of bipolar switch 460 establishes continuity between contacts 494 and 495 and/or circuit traces 416 and 418, thereby providing a bipolar activation signal to, e.g., generator 500 via cable 305.

A sensor (not shown) may be employed to determine if tissue is held between jaw members 110 and 120. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator 500 to regulate the electrosurgical energy based upon one or more pre-surgical, concurrent surgical or post surgical conditions. Various sensor mechanisms and feedback systems are described in commonly-owned U.S. Pat. No. 7,137,980 entitled "METHOD AND SYSTEM FOR CONTROLLING OUTPUT OF RF MEDICAL GENERATOR".

As seen in FIGS. 1A and 3A-C, the lower end of the movable handle 40 includes a flange 42 which is typically integrally associated with or operatively connected to movable handle 40. Flange 42 is typically T-shaped and includes a pin-like element 44 which projects laterally or transversally from a distal end thereof and is configured to engage a corresponding latch 55 disposed within fixed handle 50. More particularly, the pin 44 is configured to ride within a pre-defined channel (not explicitly shown) disposed within the latch 55 to lock the movable handle 40 relative to the fixed handle 50 upon reciprocation thereof.

The jaw members 110 and 120 are electrically isolated from one another such that electrosurgical energy can be effectively transferred through the tissue to form seal. Cable leads (not explicitly shown) are held loosely but securely along the cable path to permit rotation of the jaw members 110 and 120 about longitudinal axis "A" (See FIG. 1A). More particularly, cable leads (not explicitly shown) are fed through respective halves 80a and 80b of the rotating assembly 80 in such a manner to allow rotation of the shaft 12 (via rotation of the rotating assembly 80) in the clockwise or counter-clockwise direction without unduly tangling or twisting said cable leads. The presently disclosed cable lead feed path is envisioned to allow rotation of the rotation assembly approximately 180 degrees in either direction.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100 relative to the elongated shaft 12.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. Pat. No. 7,137,980 entitled "METHOD AND SYSTEM FOR CONTROLLING OUTPUT OF RE MEDICAL GENERATOR".

Moreover, it is envisioned that the forceps 10 may be used to cut tissue without sealing. Alternatively, a knife assembly (not explicitly shown) may be coupled to the same or alternate electrosurgical energy source to facilitate cutting of the tissue.

It is envisioned that the outer surface of the end effector assembly 100 may include a nickel-based material, coating, stamping, metal injection molding which is designed to reduce adhesion between the jaw members 110 and 120 with the surrounding tissue during activation and sealing. Moreover, it is also contemplated that the conductive surfaces 112 and 122 of the jaw members 110 and 120 may be manufactured from one (or a combination of one or more) of the following materials: nickel-chrome, chromium nitride, inconel 600, tin-nickel, and MedCoat 2000 manufactured by The Electrolizing Corporation of Ohio, Cleveland, Ohio, United States. The tissue conductive surfaces 112 and 122 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

As can be appreciated, locating switches 460, 465, and 466 on the forceps 10 has many advantages. For example, the disclosed configuration of switches 60, 65 and 66 reduces the amount of electrical cable in the operating room and eliminates the possibility of activating the wrong instrument during a surgical procedure due to "line-of-sight" activation. Switches 60, 65, and 66 may be configured such that operation thereof is mechanically or electromechanically inhibited during trigger activation, which may eliminate unintentionally activating the device during the cutting process. Switches 60, 65, and 66 may be disposed on another part of the forceps 10, e.g., the fixed handle 50, rotating assembly 80, housing 20, etc.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An electrosurgical forceps, comprising:
   a housing;
   a shaft affixed to the housing having jaw members at a distal end thereof, wherein the jaw members are configured to move relative to one another from a first position wherein the jaw members are disposed in spaced relation relative to one another to a second position wherein the jaw members are closer to one another for manipulating tissue;
a pivot pin;
a movable handle pivotable on the pivot pin and configured to cause the jaw members to move between the first and second positions;
a switch assembly included within the housing, comprising:
   a switch carrier, comprising:
      a top face;
      a top-proximal face joined to a proximal edge of the top face;
      a left face joined to a left edge of the top-proximal face;
      a right face joined to a right edge of the top-proximal face; and
      a pivot mount joined to a distal edge of the top face and configured to directly engage the pivot pin;
   a flex circuit assembly disposed on an exterior surface of the switch carrier, comprising:
      at least one monopolar switch configured to selectively activate a source of electrosurgical energy in monopolar mode;
      a monopolar safety switch configured to enable the at least one monopolar switch upon actuation of the monopolar safety switch; and
      a bipolar switch configured to selectively activate the same or a different source of electrosurgical energy in bipolar mode; and
   wherein the movable handle is configured to actuate the monopolar safety switch when the jaw members are in the second position.

2. The electrosurgical forceps of claim 1, wherein the movable handle is rotatable around the pivot pin, the movable handle further comprising a cam member adapted to actuate the monopolar safety switch when the jaw members are in the second position.

3. The electrosurgical forceps of claim 1, wherein the source of electrosurgical energy is configured to provide electrosurgical energy selected from the group consisting of monopolar electrosurgical energy and bipolar electrosurgical energy.

4. The electrosurgical forceps of claim 1, wherein the source of electrosurgical energy is operably coupled to at least one of the switch assembly or the jaw members.

5. The electrosurgical forceps of claim 1, wherein the at least one monopolar switch comprises at least two monopolar switches coupled in parallel.

6. The electrosurgical forceps of claim 1, wherein the monopolar safety switch is coupled in series with the at least one monopolar switch.

* * * * *